United States Patent

Stevens

(10) Patent No.: US 9,076,038 B2
(45) Date of Patent: Jul. 7, 2015

(54) DETECTION OF NON-COMPLIANCE PATTERNS IN PRESCRIBED MEDICATION DOSES

(75) Inventor: Gerard Stevens, Huntleys Point (AU)

(73) Assignee: Manrex Pty. Ltd., Leichardt, New South Wales (AU)

( * ) Notice: Subject to any disclaimer, the term of this patent is extended or adjusted under 35 U.S.C. 154(b) by 99 days.

(21) Appl. No.: 13/813,118

(22) PCT Filed: Aug. 16, 2011

(86) PCT No.: PCT/AU2011/001030
§ 371 (c)(1),
(2), (4) Date: Jan. 29, 2013

(87) PCT Pub. No.: WO2012/021920
PCT Pub. Date: Feb. 23, 2012

(65) Prior Publication Data
US 2013/0129186 A1    May 23, 2013

(30) Foreign Application Priority Data

Aug. 16, 2010   (AU) ................... 2010903661

(51) Int. Cl.
*G06K 9/00* (2006.01)
*G06F 19/00* (2011.01)
*G06Q 50/24* (2012.01)
*A61J 1/03* (2006.01)

(52) U.S. Cl.
CPC ............ *G06K 9/00624* (2013.01); *A61J 1/035* (2013.01); *G06F 19/3462* (2013.01); *A61J 2200/30* (2013.01); *G06Q 50/24* (2013.01)

(58) Field of Classification Search
None
See application file for complete search history.

(56) References Cited

U.S. PATENT DOCUMENTS

| 2004/0167408 A1 | 8/2004 | Ashida et al. |
| 2008/0047969 A1 | 2/2008 | Farhan et al. |
| 2008/0119958 A1 | 5/2008 | Bear et al. |

OTHER PUBLICATIONS

International Search Report, PCT/AU2011/001030, completed Nov. 2, 2011, mailed Nov. 8, 2011, 2 pages.

*Primary Examiner* — Mark Roz
(74) *Attorney, Agent, or Firm* — Chernoff, Vilhauer, McClung & Stenzel LLP

(57) ABSTRACT

Apparatus for detecting non-compliance patterns on a series of used blister sheets previously returned by the same patient, reads a code (2) on each blister sheet (1) providing, inter alia, information relating to the position of each blister on the blister sheet. This information is passed by the code reader (4) through a key (15) to an image (5) of the blister sheet appearing on one-half (14) of a split screen (6). The screen (14) displays a picture of a blister sheet with its blister positions marked by dots or rings (8). By means of the key (15), which may take the form of a joystick, an image of a disc (9) can be placed over each of the blister positions where an unopened blisters occurs. The image of the blister sheet together with the discs is then transferred by operation of a key (10) to the second half (11) of the split screen (6) screen where it is superimposed on a slightly offset stack (13) of used blister sheets previously returned by the same patient. The positions of the discs (9) are compared by the apparatus with corresponding positions on previously returned blister sheets and, if a coincidence is detected, the apparatus produces a change in the appearance of the corresponding disc on the blister sheet on the top of the stack. A change in a disc appearance suggests that there may be a pattern of non-compliance that can then be investigated further.

5 Claims, 2 Drawing Sheets

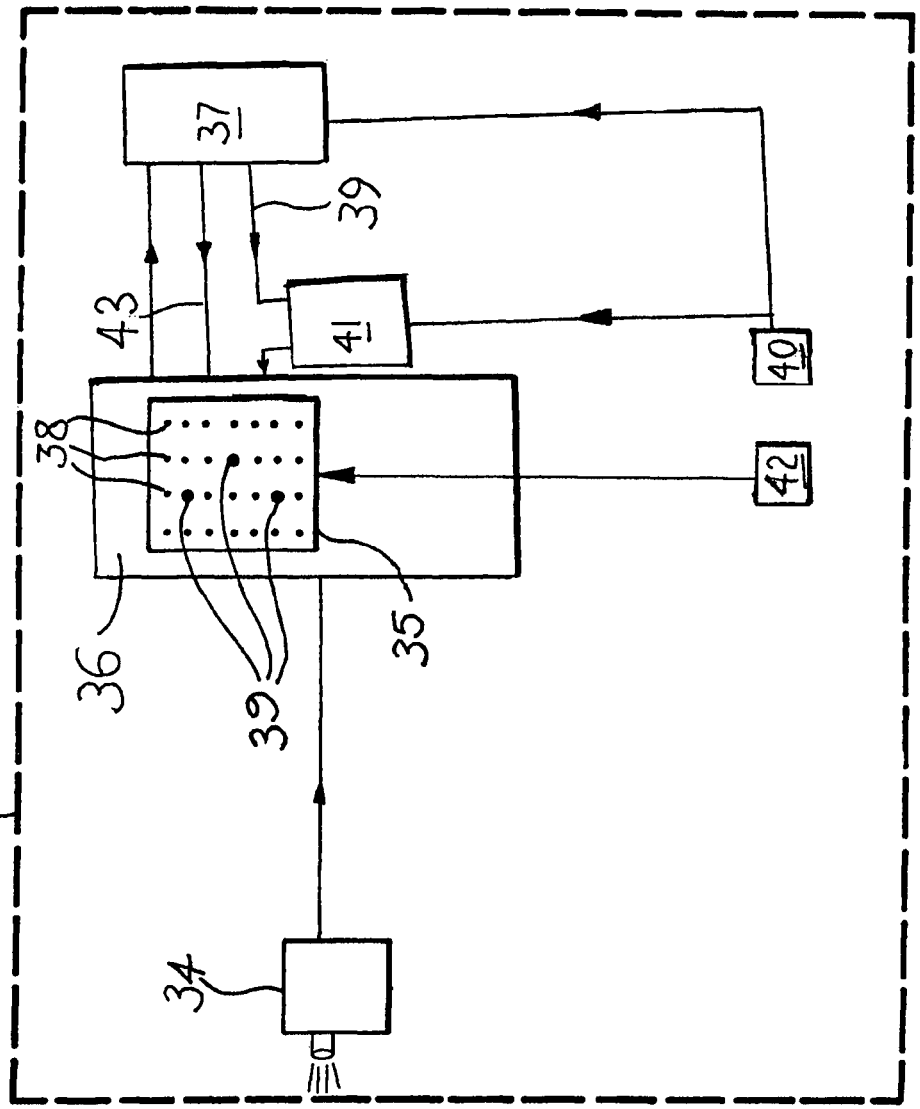

Figure 1:
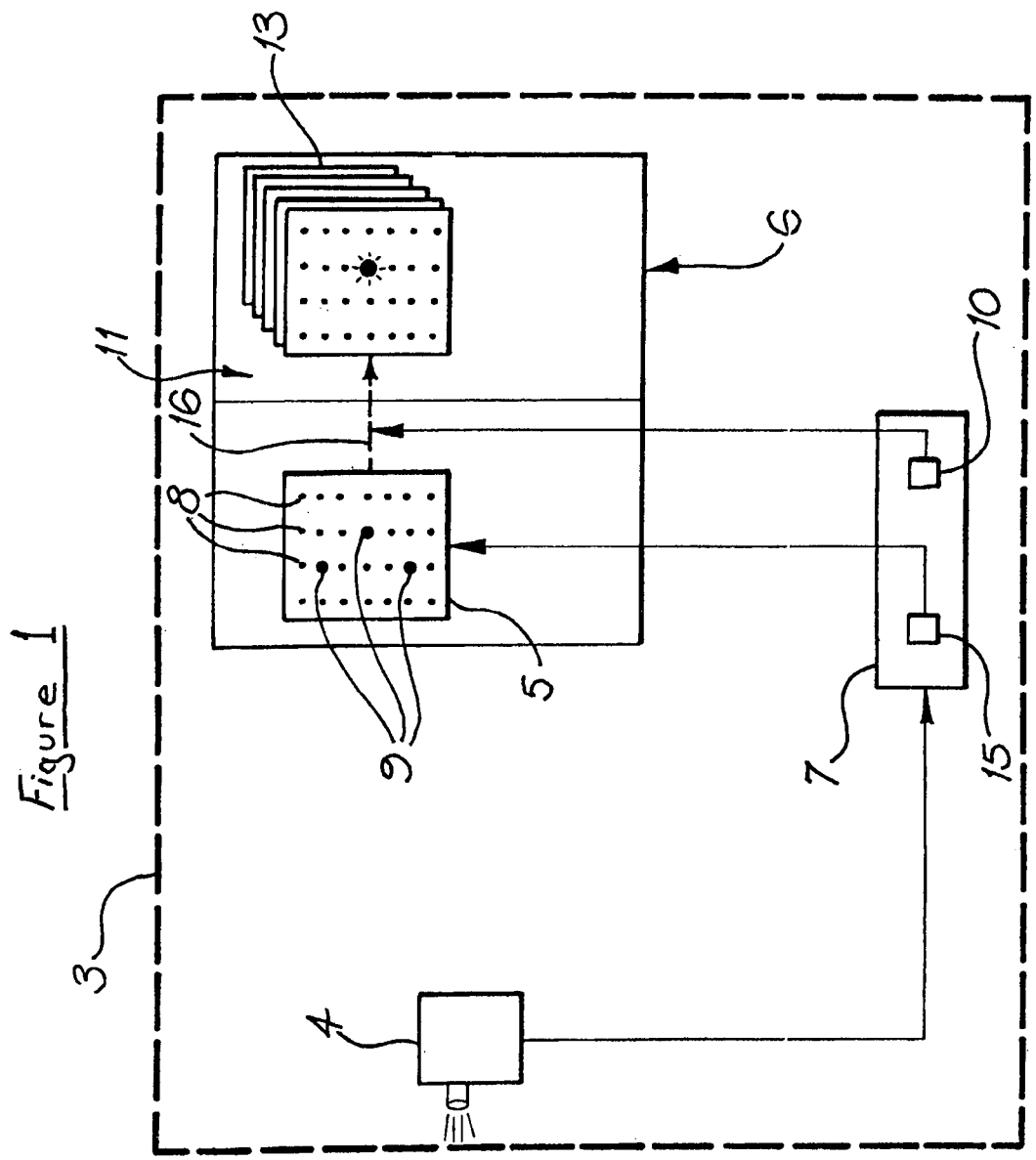

DETECTION OF NON-COMPLIANCE PATTERNS IN PRESCRIBED MEDICATION DOSES

CROSS-REFERENCE TO RELATED APPLICATION

This is a national stage application filed under 35 USC 371 based on International Application No. PCT/AU2011/001030 filed Aug. 16, 2011, and claims priority under 35 USC 119 of Australian Patent Application No. 2010903661 filed Aug. 16, 2010.

FIELD OF THE INVENTION

THIS INVENTION relates to the detection of a recurring failure of a patient to take prescribed medication doses at a particular time on a particular day. More specifically it is concerned with monitoring a sequence of blister packages returned by the patient to a pharmacist, and identifying the existence of a repeating pattern of non-compliance. The non-compliance relates to medical instructions given by a prescribing doctor and concerning the administration of the medication doses to the patient.

BACKGROUND AND STATE OF THE ART

There are a variety of reasons why a patient may not take prescribed doses of medication at a required time. This may have serious consequences for the patient. One such reason may be the result of a patient having a poor memory. Another reason may be that a routine followed by the patient is interrupted so that the need for the administration of the medication is forgotten. Such interruptions may be random, however it has been noticed that there is sometimes a recurring pattern of non-compliance and it is then advisable to investigate the reason for the non-compliance so that steps can be taken to avoid it in future.

Non-compliance of a patient is apparent when a pharmacist notices that, not for The first time, a used package of blisters containing prescribed medication doses and intended to cover a period of use, such as a week, is being returned by a particular patient with some of the blisters unopened. Should the pharmacist find the time to compare the used blister packages returned by a particular patient with one another, it might be noticed that the same blisters on different blister packages are being left unopened on a significant number of occasions. However a busy pharmacist may be disinclined to spend the time involved in searching for a recurring pattern of non-compliance as the investigation involved takes time and the incidence of non-complying blister packages having a recurring pattern of unopened blisters is relatively small.

OBJECT OF THE INVENTION

An object of this invention is to simplify the identification of a recurring pattern of non-compliance in a number of used blister packages returned by a patient.

THE INVENTION

In accordance with the broadest aspect of this invention there is provided apparatus for enabling an operator to detect a recurring pattern of non-compliance in used blister packages returned by a particular patient at the end of their respective periods of use, such apparatus having a store for retaining data significant of the positions of unopened blisters in blister packages previously returned by the same patient, a screen on which the operator can mark the positions of each unopened blister on a newly-returned blister package from the same patient, first circuitry for recording in the store each unopened blister position identified by the operator and appearing on a newly-returned blister package, and second circuitry operating to mark on the screen a coincidence in position between an unopened blister on the newly-returned blister package and an unopened blister position on a previously returned blister package from the same patient.

In accordance with a narrower aspect of the invention, apparatus for detecting a recurring pattern of non-compliance in used blister packages returned by a particular patient at the end of their respective periods of use, comprises a screen for recording the positions of unopened blisters on a newly-returned blister package, the screen having associated circuitry for supplying a store with data significant of the positions of unopened blisters and for displaying on the screen superimposed images of a sequence of returned packages with the positions of coinciding unopened blisters uniquely marked to indicate that a recurring pattern of non-compliance exists which may be worthy of further investigation.

In accordance with a further aspect of the invention apparatus for detecting a recurring pattern of non-compliance in used blister packages returned by a particular patient at the end of their respective periods of use, such having a screen with associated first circuitry enabling an operator of the apparatus to indicate on the screen the position at which a, or each unopened blister is located on a newly-returned blister package from a particular patient, a store for retaining information denoting the positions of unopened blisters in each of a succession of blister packages returned previously by the same patient, and further circuitry for uniquely marking on a displayed image of a newly-returned blister package the existence and frequency of a coincidence in position of an unopened blister in the package on it with the position of an unopened blister on one or more previously-returned blister packages from the same patient.

PREFERRED FEATURES OF THE INVENTION

Preferably the screen provides images of a succession of returned blister packages superimposed on one another, suitably with a slight offset, to enable the operator of the apparatus to identify quickly a recurring pattern of unopened blisters on respective blister packages. This may be denoted by a change in colour of the unopened blister position. Alternatively or additionally the colour of the unopened blister at that position may be intensified with an increase in intensity signifying the number of unopened blisters at that position. The position at which unopened blisters coincide may also be signified by displaying a disc image at that position, the diameter of the disc noticeably increasing with increase in the number of unopened blisters at that position.

It will be appreciated that other means may be used to display the positions of unopened blisters on the screen, and those mentioned above are simply examples of what may be used for this purpose. However, it is preferred to change the intensity of the colour at the position of the superimposed unopened blisters so that it becomes more intense with an increasing likelihood of a recurring pattern of non-compliance being present.

INTRODUCTION TO THE ACCOMPANYING DRAWINGS

The invention will now be described, by way of example and with reference to the two accompanying drawings in which:

In the drawings

FIG. 1 shows in a greatly simplified, block schematic form a first embodiment of apparatus for carrying out the invention; and, FIG. 2 also shows in a greatly simplified block schematic form a second embodiment of apparatus for carrying out the invention.

DESCRIPTION AND USE OF THE FIRST EMBODIMENT OF APPARATUS

Referring to the FIG. 1, a used blister package 1 returned to a pharmacist by a patient at the end of its period of use, carries a bar code 2 containing a large amount of data identifying the patient, the prescribed medication doses in the blister package and other items of information provided by a prescribing doctor and the pharmacist who made up the blister package. Only the essential parts of the apparatus for detecting non-compliance patterns is shown within the pecked outline 3. The apparatus is provided with a bar code reader 4 which enables the pharmacist to down-load into the apparatus the coded information from the bar code 2 on the returned blister package 1. A store 18 in the apparatus retains data significant of the positions of unopened blisters on previously returned blister packages from the same patient.

The apparatus 3 has a touch-sensitive screen 6 that displays an image 5 of a newly-returned blister package obtained from the bar code 2. This image 5 appears on the left-hand side 14 of a vertical split 10 in the the centre of the screen 6 as diagrammatically illustrated in the figure. The positions of the blisters on the package are denoted on the screen by an array of rings or spots 8.

As the screen is touch-sensitive, the operator of the apparatus can touch those blister positions corresponding to the positions of unopened blisters on a newly-returned blister package 1. The effect of touching the screen is to cause an image 5 of an enlarged disc 9, which may also be distinctively coloured, to be superimposed on the corresponding blister position to denote an unopened blister. When the operator is satisfied that all of the unopened blister positions have been correctly marked on the image of the blister package on the screen 5, a transfer switch 15 is closed to move the image of the blister package from the left-hand half of the screen to the right-hand half where it is superimposed on the images of previously-returned blister images. This action also causes the positions of the unopened blisters to be transferred to the data store 18 for future comparisons to be made.

FIG. 1 shows diagrammatically the existence on the screen of three unopened blister positions which appear on a newly-returned blister package.

When the positions of all of the unopened blisters have been marked by discs 9 on the blister package image 5, a transfer key 10 on the keyboard 7 is operated to transfer an image of the blister package together with its coloured discs 9, from the left-hand half 14 of the screen to the right-hand half 11, as shown by the broken thick arrow 16. This action superimposes the image 5 onto the top of a stack 13 of previously returned blister packages as shown in the figure. It will be noticed that the images of the blister packages forming the stack are slightly offset with respect to one another to give the operator an idea of the number of returned blister packages being compared.

If there is a coincidence in the position of any of the unopened blisters on two or more of the blister packages in the stack, the intensity of the colour of the disc marking the position of the coincidence, is arranged to noticeably increase. Also, this coincidence may be denoted by a change in the actual colour of the disc or discs at the positions of the coinciding unopened blisters. The diameter of the disc on the top of the stack may also arranged to increase with the number of unopened blisters at the same position on the returned blister packages. Likewise if the disc is coloured, the intensity of its colour can be arranged to increase also. This gives the operator an idea of the frequency of the recurrence of unopened coinciding blister packages.

The existence of a recurring non-compliance pattern is thus immediately apparent to the operator by the size and the colour intensity of the disc on the top of the stack. The reason for the non-compliance can then be explored and appropriate steps taken to prevent it recurring in future.

DESCRIPTION OF SECOND EMBODIMENT OF THE INVENTION

FIG. 2 shows apparatus for detecting the possibility of a recurring pattern of non-compliance in a series of used blister packages returned from the same patient.

A blister package newly returned by a patient is shown at 31. It has a bar code 32 printed on it giving all of the relevant details of the identity of the patient, the prescribed medications in the blisters of the package when first given to the patient, and a record of the doctor who prescribed the medication doses intended for filling the blisters of the package, the identity of the pharmacist who prepared the blister package for the patient, the pharmacy where the packaging was done and other relevant information.

The newly returned package h31 has the bar code 32 read by a bar code reader 34 forming part of the apparatus which is shown within the pecked outline 33. The various components of the apparatus not directly relevant to the carrying out of the invention are not shown, as to do otherwise would unnecessarily burden the description of the figure which shows only those components which are essential. Also the components are in block form as they would be considered to be easily provided by those skilled in the art of computer technologies.

The bar code 32 is transferred to a bar-code reader 34 in the apparatus and fed to an image of the basic blister package 35 appearing on a touch-sensitive screen 36. The image of the package on the screen has the positions of its blisters denoted by small rings or dots 38.

An operator of the apparatus, usually a pharmacist or an assistant, views the screen 36 and touches the blister positions corresponding to the positions of any unopened blisters on a newly-returned blister package. Each time he touches the screen at a blister position, a mark appear there, either a large disc or a coloured marking of some kind to indicate to the operator that the touch has been recorded. When the operator is satisfied that all of the unopened blisters have been correctly marked on the screen a key 42 on the apparatus is operated and the information concerning the package and the unopened blisters is transmitted through first circuitry 38 to a data store 37.

The apparatus can be set up to enable the store 37 to monitor the information retained in it either automatically or only when required by the operator, to see whether a recurring pattern of unopened blisters on previously-returned blister packages is present. If this is to be done automatically, the store sends an appropriate signal through second circuitry 43 when a recurring pattern is detected. The screen 36 is then marked appropriately to warn the operator of this occurrence.

On the other hand the operator may be provided with a key 42 which operates to transfers the signal previously sent through the circuitry 43, to the circuitry 39 which is opened by a switch 41 actuated by the key 42. The actuation of the key 42 causes the screen to be again appropriately marked in a distinctive way to denote the positions of a recurring pattern of unopened blisters on returned blister packages. Information concerning these unopened blisters may also be presented on the screen to enable a decision to be made concerning whether an investigation should be carried out to determine a possible reason for the recurrent pattern of unopened blisters.

The invention claimed is:

1. Apparatus for detecting a recurring pattern of non-compliance in used blister packages returned by a particular patient at the end of their respective periods of use, comprising a screen for recording the positions of unopened blisters on a newly-returned blister package, the screen being split to allow the positions of unopened blisters to be marked on a blister package image on one part of the screen, and the screen having means for moving that image across the split to a position at which it is superimposed on the image of a previously returned blister package originating from the same patient, and the screen having associated circuitry for supplying a store with data significant of the positions of unopened blisters and for displaying on the screen superimposed images of a sequence of returned packages with the positions of coinciding unopened blisters uniquely marked to indicate that a recurring pattern of non-compliance exists which may be worthy of further investigation.

2. Apparatus as set forth in claim 1, in which the unique marking takes the form of a colour change denoting the position of an unopened blister.

3. Apparatus as set forth in claim 1, in which the colour change appears as a change in the intensity of the colour of the marker.

4. Apparatus as set forth in claim 1, in which the coincidence of two unopened blisters on respective blister package images is denoted by a change in the size of a marker on the screen at the position of the coinciding unopened blisters.

5. Apparatus as set forth in claim 1 in which the image moved across the split screen is superimposed on previous blister package images to provide a picture in the form of an offset stack of previously returned blister packages originating from the same patient.

* * * * *